United States Patent
Ledbetter et al.

(10) Patent No.: US 11,360,164 B2
(45) Date of Patent: Jun. 14, 2022

(54) INTEGRATED MAGNETOMETER ARRAYS FOR MAGNETOENCEPHALOGRAPHY (MEG) DETECTION SYSTEMS AND METHODS

(71) Applicant: HI LLC, Los Angeles, CA (US)

(72) Inventors: Micah Ledbetter, Sunnyvale, CA (US); Hooman Mohseni, Wilmette, IL (US); Jamu Alford, Simi Valley, CA (US); Ethan Pratt, Santa Clara, CA (US); Daniel Sobek, Portola Valley, CA (US)

(73) Assignee: HI LLC, Los Angeles, CA (US)

( * ) Notice: Subject to any disclaimer, the term of this patent is extended or adjusted under 35 U.S.C. 154(b) by 74 days.

(21) Appl. No.: 16/820,131

(22) Filed: Mar. 16, 2020

(65) Prior Publication Data
US 2020/0309873 A1    Oct. 1, 2020

Related U.S. Application Data

(60) Provisional application No. 62/858,636, filed on Jun. 7, 2019, provisional application No. 62/826,045, filed on Mar. 29, 2019.

(51) Int. Cl.
*G01R 33/26* (2006.01)

(52) U.S. Cl.
CPC .................... *G01R 33/26* (2013.01)

(58) Field of Classification Search
CPC .. G01R 33/26; G01R 33/0094; G01R 33/032; A61B 5/245; G01N 24/006
See application file for complete search history.

(56) References Cited

U.S. PATENT DOCUMENTS 3,173,082 A    3/1965  Bell et al.
3,257,608 A    6/1966  Bell et al.
(Continued)

FOREIGN PATENT DOCUMENTS

CN    104730484    6/2015
CN    107562188    1/2018
(Continued)

OTHER PUBLICATIONS

Arjen Stolk, Ana Todorovic, Jan-Mathijs Schoffelen, and Robert Oostenveld. "Online and offline tools for head movement compensation in MEG." Neuroimage 68 (2013): 39-48.
(Continued)

*Primary Examiner* — Jay Patidar
(74) *Attorney, Agent, or Firm* — Branch Partners PLLC; Bruce E. Black

(57) ABSTRACT

An array of optically pumped magnetometers includes a vapor cell arrangement having a wafer defining one or more cavities and alkali metal atoms disposed in the cavities to provide an alkali metal vapor; an array of light sources, each of the light sources arranged to illuminate a different portion of the one or more cavities of the vapor cell arrangement with light; at least one mirror arranged to reflect the light from the array of light sources after the light passes through the one or more cavities of the vapor cell arrangement; and an array of detectors to receive light reflected by the at least one mirror, wherein each of the detectors is arranged to receive light originating from one of the light sources.

18 Claims, 6 Drawing Sheets

(56) References Cited

U.S. PATENT DOCUMENTS

| | | |
|---|---|---|
| 3,495,161 A | 2/1970 | Bell |
| 3,501,689 A | 3/1970 | Robbiano |
| 3,513,381 A | 5/1970 | Happer, Jr. |
| 4,193,029 A | 3/1980 | Cioccio et al. |
| 4,951,674 A | 8/1990 | Zanakis et al. |
| 5,189,368 A | 2/1993 | Chase |
| 5,192,921 A | 3/1993 | Chantry et al. |
| 5,225,778 A | 7/1993 | Chaillout et al. |
| 5,254,947 A | 10/1993 | Chaillout et al. |
| 5,309,095 A | 5/1994 | Ahonen et al. |
| 5,442,289 A | 8/1995 | Dilorio et al. |
| 5,444,372 A | 8/1995 | Wikswo, Jr. et al. |
| 5,471,985 A | 12/1995 | Warden |
| 5,506,200 A | 4/1996 | Hirschkoff et al. |
| 5,526,811 A | 6/1996 | Lypchuk |
| 5,713,354 A | 2/1998 | Warden |
| 6,144,872 A | 11/2000 | Graetz |
| 6,339,328 B1 | 1/2002 | Keene et al. |
| 6,472,869 B1 | 10/2002 | Upschulte et al. |
| 6,665,553 B2 | 12/2003 | Kandori et al. |
| 6,806,784 B2 | 10/2004 | Hollberg et al. |
| 6,831,522 B2 | 12/2004 | Kitching et al. |
| 7,038,450 B2 | 5/2006 | Romalis et al. |
| 7,102,451 B2 | 9/2006 | Happer et al. |
| 7,145,333 B2 | 12/2006 | Romalis et al. |
| 7,521,928 B2 | 4/2009 | Romalis et al. |
| 7,656,154 B2 | 2/2010 | Kawabata et al. |
| 7,826,065 B1 | 11/2010 | Okandan et al. |
| 7,872,473 B2 | 1/2011 | Kitching et al. |
| 7,994,783 B2 | 8/2011 | Ledbetter et al. |
| 8,054,074 B2 | 11/2011 | Ichihara et al. |
| 8,212,556 B1 | 7/2012 | Schwindt et al. |
| 8,258,884 B2 | 9/2012 | Borwick, III et al. |
| 8,319,156 B2 | 11/2012 | Borwick, III et al. |
| 8,334,690 B2 | 12/2012 | Kitching et al. |
| 8,373,413 B2 | 2/2013 | Sugioka |
| 8,405,389 B2 | 3/2013 | Sugioka et al. |
| 8,587,304 B2 | 11/2013 | Budker et al. |
| 8,836,327 B2 | 9/2014 | French et al. |
| 8,906,470 B2 | 12/2014 | Overstolz et al. |
| 8,941,377 B2 | 1/2015 | Mizutani et al. |
| 9,084,549 B2 | 7/2015 | Desain et al. |
| 9,095,266 B1 | 8/2015 | Fu |
| 9,116,201 B2 | 8/2015 | Shah et al. |
| 9,140,590 B2 | 9/2015 | Waters et al. |
| 9,140,657 B2 | 9/2015 | Ledbetter et al. |
| 9,169,974 B2 | 10/2015 | Parsa et al. |
| 9,244,137 B2 | 1/2016 | Kobayashi et al. |
| 9,291,508 B1 | 3/2016 | Biedermann et al. |
| 9,343,447 B2 | 5/2016 | Parsa et al. |
| 9,366,735 B2 | 6/2016 | Kawabata et al. |
| 9,383,419 B2 | 7/2016 | Mizutani et al. |
| 9,395,425 B2 | 7/2016 | Diamond et al. |
| 9,417,293 B2 | 8/2016 | Schaffer et al. |
| 9,429,918 B2 | 8/2016 | Parsa et al. |
| 9,568,565 B2 | 2/2017 | Parsa et al. |
| 9,575,144 B2 | 2/2017 | Kornack et al. |
| 9,601,225 B2 | 3/2017 | Parsa et al. |
| 9,638,768 B2 | 5/2017 | Foley et al. |
| 9,639,062 B2 | 5/2017 | Dyer et al. |
| 9,677,905 B2 | 6/2017 | Waters et al. |
| 9,726,626 B2 | 8/2017 | Smith et al. |
| 9,726,733 B2 | 8/2017 | Smith et al. |
| 9,791,536 B1 | 10/2017 | Alem et al. |
| 9,829,544 B2 | 11/2017 | Bulatowicz |
| 9,846,054 B2 | 12/2017 | Waters et al. |
| 9,851,418 B2 | 12/2017 | Wolf et al. |
| 9,869,731 B1 | 1/2018 | Hovde et al. |
| 9,915,711 B2 | 3/2018 | Kornack et al. |
| 9,927,501 B2 | 3/2018 | Kim et al. |
| 9,948,314 B2 | 4/2018 | Dyer et al. |
| 9,964,609 B2 | 5/2018 | Ichihara et al. |
| 9,964,610 B2 | 5/2018 | Shah et al. |
| 9,970,999 B2 | 5/2018 | Larsen et al. |
| 9,995,800 B1 | 6/2018 | Schwindt et al. |
| 10,024,929 B2 | 7/2018 | Parsa et al. |
| 10,088,535 B1 | 10/2018 | Shah |
| 10,162,016 B2 | 12/2018 | Gabrys et al. |
| 10,194,865 B2 | 2/2019 | Le et al. |
| 10,314,508 B2 | 6/2019 | Desain et al. |
| 10,371,764 B2 | 8/2019 | Morales et al. |
| 10,772,561 B2 | 9/2020 | Donaldson |
| 2004/0232912 A1 | 11/2004 | Tsukamoto et al. |
| 2005/0007118 A1 | 1/2005 | Kitching et al. |
| 2005/0046851 A1 | 3/2005 | Riley, Jr. et al. |
| 2005/0206377 A1 | 9/2005 | Romalis et al. |
| 2007/0076776 A1 | 4/2007 | Lust et al. |
| 2007/0120563 A1 | 5/2007 | Kawabata et al. |
| 2007/0167723 A1 | 7/2007 | Park et al. |
| 2007/0205767 A1 | 9/2007 | Xu et al. |
| 2009/0079426 A1 | 3/2009 | Anderson |
| 2009/0101806 A1 | 4/2009 | Masuda |
| 2010/0219820 A1 | 9/2010 | Skidmore et al. |
| 2011/0062956 A1 | 3/2011 | Edelstein et al. |
| 2012/0112749 A1 | 5/2012 | Budker et al. |
| 2013/0082700 A1 | 4/2013 | Mizutani et al. |
| 2013/0082701 A1 | 4/2013 | Mizutani et al. |
| 2013/0265042 A1 | 10/2013 | Kawabata et al. |
| 2014/0121491 A1 | 5/2014 | Zhang |
| 2014/0306700 A1 | 10/2014 | Kamada et al. |
| 2014/0354275 A1 | 12/2014 | Sheng et al. |
| 2015/0022200 A1 | 1/2015 | Ichihara et al. |
| 2015/0054504 A1 | 2/2015 | Ichihara et al. |
| 2015/0378316 A1 | 12/2015 | Parsa et al. |
| 2016/0061913 A1 | 3/2016 | Kobayashi et al. |
| 2016/0116553 A1 | 4/2016 | Kim et al. |
| 2016/0223627 A1 | 8/2016 | Shah et al. |
| 2016/0291099 A1* | 10/2016 | Ueno ............... A61B 5/055 |
| 2016/0313417 A1 | 10/2016 | Kawabata et al. |
| 2017/0023653 A1 | 1/2017 | Kobayashi et al. |
| 2017/0023654 A1 | 1/2017 | Kobayashi et al. |
| 2017/0067969 A1 | 3/2017 | Butters et al. |
| 2017/0199138 A1 | 7/2017 | Parsa et al. |
| 2017/0199251 A1 | 7/2017 | Fujii et al. |
| 2017/0261564 A1 | 9/2017 | Gabrys et al. |
| 2017/0331485 A1 | 11/2017 | Gobet et al. |
| 2017/0343617 A1 | 11/2017 | Manickam et al. |
| 2017/0343695 A1 | 11/2017 | Stetson et al. |
| 2017/0356969 A1 | 12/2017 | Ueno |
| 2017/0360322 A1 | 12/2017 | Ueno |
| 2017/0363695 A1 | 12/2017 | Ueno |
| 2018/0003777 A1 | 1/2018 | Sorensen et al. |
| 2018/0038921 A1 | 2/2018 | Parsa et al. |
| 2018/0100749 A1 | 4/2018 | Waters et al. |
| 2018/0128885 A1 | 5/2018 | Parsa et al. |
| 2018/0156875 A1 | 6/2018 | Herbsommer et al. |
| 2018/0219353 A1 | 8/2018 | Shah |
| 2018/0238974 A1 | 8/2018 | Shah et al. |
| 2018/0313908 A1 | 11/2018 | Knappe et al. |
| 2018/0313913 A1 | 11/2018 | DeNatale et al. |
| 2018/0372813 A1 | 12/2018 | Bulatowicz et al. |
| 2019/0391213 A1 | 12/2019 | Alford |
| 2020/0002802 A1* | 1/2020 | Kitching ............ B23K 1/20 |
| 2020/0025844 A1 | 1/2020 | Alford et al. |
| 2020/0057115 A1 | 2/2020 | Jiménez-Martínez et al. |
| 2020/0057116 A1 | 2/2020 | Zorzos et al. |
| 2020/0064421 A1 | 2/2020 | Kobayashi et al. |
| 2020/0072916 A1 | 3/2020 | Alford et al. |
| 2020/0088811 A1 | 3/2020 | Mohseni |
| 2020/0241094 A1 | 7/2020 | Alford |
| 2020/0256929 A1 | 8/2020 | Ledbetter et al. |
| 2020/0309873 A1 | 10/2020 | Ledbetter et al. |
| 2020/0334559 A1 | 10/2020 | Anderson et al. |
| 2020/0341081 A1 | 10/2020 | Mohseni et al. |
| 2020/0381128 A1 | 12/2020 | Pratt et al. |
| 2020/0400763 A1 | 12/2020 | Pratt |
| 2021/0063510 A1 | 3/2021 | Ledbetter |

FOREIGN PATENT DOCUMENTS

| | | |
|---|---|---|
| EP | 2738627 A3 | 6/2014 |
| EP | 2380029 B1 | 10/2015 |
| EP | 3037836 B1 | 9/2017 |
| JP | 2016109665 | 6/2016 |

(56) References Cited

FOREIGN PATENT DOCUMENTS

| | | |
|---|---|---|
| JP | 2018004462 | 1/2018 |
| WO | 2005/081794 | 9/2005 |
| WO | 2014/031985 | 2/2014 |
| WO | 2017/095998 | 6/2017 |

OTHER PUBLICATIONS

Bagherzadeh, Yasaman, Daniel Baldauf, Dimitrios Pantazis, and Robert Desimone. "Alpha synchrony and the neurofeedback control of spatial attention." Neuron 105, No. 3 (2020): 577-587.

Tierney, T. M., Holmes, N., Meyer, S. S., Boto, E., Roberts, G., Leggett, J., . . . Barnes, G. R. (2018). Cognitive neuroscience using wearable magnetometer arrays: Non-invasive assessment of language function. NeuroImage, 181, 513-520.

Hill RM, Boto E, Holmes N, et al. A tool for functional brain imaging with lifespan compliance [published correction appears in Nat Commun. Dec. 4, 2019;10(1):5628]. NatCommun. 2019;10(1):4785. Published Nov. 5, 2019. doi:10.1038/s41467-019-12486-x.

Zetter, R., Iivanainen, J. & Parkkonen, L. Optical Co-registration of MRI and On-scalp MEG. Sci Rep 9, 5490 (2019). https://doi.org/10.1038/s41598-019-41763-4.

Garrido-Jurado, Sergio, Rafael Muñoz-Salinas, Francisco José Madrid-Cuevas and Manuel J. Marín-Jiménez. "Automatic generation and detection of highly reliable fiducial markers under occlusion." Pattern Recognit. 47 (2014): 2280-2292.

Hill RM, Boto E, Rea M, et al. Multi-channel whole-head OPM-MEG: Helmet design and a comparison with a conventional system [published online ahead of print, May 29, 2020]. Neuroimage. 2020;219:116995. doi: 10.1016/j.neuroimage.2020.116995.

V. Kazemi and J. Sullivan, "One millisecond face alignment with an ensemble of regression trees," 2014 IEEE Conference on Computer Vision and Pattern Recognition, Columbus, OH, 2014, pp. 1867-1874, doi: 10.1109/CVPR.2014.241.

Holmes, N., Tierney, T.M., Leggett, J. et al. Balanced, bi-planar magnetic field and field gradient coils for field compensation in wearable magnetoencephalography. Sci Rep 9, 14196 (2019).

N. Holmes, J. Leggett, E. Boto, G. Roberts, R.M. Hill, T.M. Tierney, V. Shah, G.R. Barnes, M.J. Brookes, R. Bowtell A bi-planar coil system for nulling background magnetic fields in scalp mounted magnetoencephalography Neuroimage, 181 (2018), pp. 760-774.

J. M. Leger et al., In-flight performance of the Absolute Scalar Magnetometer vector mode on board the Swarm satellites, Earth, Planets, and Space (2015) 67:57.

Alexandrov, E. B., Balabas, M. V., Kulyasov, V. N., Ivanov, A. E., Pazgalev, A. S., Rasson, J. L., . . . (2004). Three-component variometer based on a scalar potassium sensor. Measurement Science and Technology, 15(5), 918-922.

Gravrand, O., Khokhlov, A., & JL, L. M. (2001). On the calibration of a vectorial 4He pumped magnetometer. Earth, planets and space, 53 (10), 949-958.

Borna, Amir & Carter, Tony & Colombo, Anthony & Jau, Y-Y & McKay, Jim & Weisend, Michael & Taulu, Samu & Stephen, Julia & Schwindt, Peter. (2018). Non-Invasive Functional-Brain-Imaging with a Novel Magnetoencephalography System. 9 Pages.

Vrba J, Robinson SE. Signal processing in magnetoencephalography. Methods. 2001;25(2):249-271. doi:10.1006/meth.2001.1238.

Uusitalo M and Ilmoniemi R., 1997, Signal-space projection method for separating MEG or EEG into components Med. Biol. Comput (35) 135-140.

Taulu S and Kajola M., 2005, Presentation of electromagnetic multichannel data: the signal space separation method. J. Appl. Phys. (97) 124905 (2005).

Taulu S, Simola J and Kajola M., 2005, Applications of the signal space separation method. IEEE Trans. Signal Process. (53) 3359-3372 (2005).

Taulu S, Simola J., 2006, Spatiotemporal signal space separation method for rejecting nearby interference in MEG measurements. Phys. Med. Biol. (51) 1759-1768 (2006).

Johnson, et al., Magnetoencephalography with a two-color pump-probe, fiber-coupled atomic magnetometer, Applied Physics Letters 97, 243703 2010.

Zhang, et al., Magnetoencephalography using a compact multichannel atomic magnetometer with pump-probe configuration, AIP Advances 8, 125028 (2018).

Xia, H. & Ben-Amar Baranga, Andrei & Hoffman, D. & Romalis, Michael. (2006). Magnetoencephalography with an atomic magnetometer. Applied Physics Letters—Appl Phys Lett. 89. 10.1063/1.2392722.

Ilmoniemi, R. (2009). The triangle phantom in magnetoencephalography. In 24th Annual Meeting of Japan Biomagnetism and Bioelecctromagnetics Society, Kanazawa, Japan, 28.29.5.2009 (pp. 6263).

Oyama D. Dry phantom for magnetoencephalography—Configuration, calibration, and contribution. J Neurosci Methods. 2015;251:24-36. doi: 0.1016/j.jneumeth.2015.05.004.

Chutani, R., Maurice, V., Passilly, N. et al. Laser light routing in an elongated micromachined vapor cell with diffraction gratings for atomic clock applications Sci Rep 5, 14001 (2015). https://doi.org/10.1038/srep14001.

Eklund, E. Jesper, Andrei M. Shkel, Svenja Knappe, Elizabeth A. Donley and John Kitching. "Glass-blown spherical microcells for chip-scale atomic devices." (2008).

Jiménez-Martínez R, Kennedy DJ, Rosenbluh M, et al. Optical hyperpolarization and NMR detection of 129Xe on a microfluidic chip. Nat Commun. 2014;5:3908. Published May 20, 2014. doi:10.1038/ncomms4908.

Boto, Elena, Sofie S. Meyer, Vishal Shah, Orang Alem, Svenja Knappe, Peter Kruger, T. Mark Fromhold, et al. "A New Generation of Magnetoencephalography: Room Temperature Measurements Using Optically-Pumped Magnetometers." NeuroImage 149 (Apr. 1, 2017): 404-14.

Bruno, A. C., and P. Costa Ribeiro. "Spatial Fourier Calibration Method for Multichannel SQUID Magnetometers." Review of Scientific Instruments 62, No. 4 (Apr. 1, 1991): 1005-9.

Chella, Federico, Filippo Zappasodi, Laura Marzetti, Stefania Della Penna, and Vittorio Pizzella. "Calibration of a Multichannel MEG System Based on the Signal Space Separation Method." Physics in Medicine and Biology 57 (Jul. 13, 2012): 4855-70.

Pasquarelli, A, M De Melis, Laura Marzetti, Hans-Peter Müller, and S N Erné. "Calibration of a Vector-MEG Helmet System." Neurology & Clinical Neurophysiology□: NCN 2004 (Feb. 1, 2004): 94.

Pfeiffer, Christoph, Lau M. Andersen, Daniel Lundqvist, Matti Hämäläinen, Justin F. Schneiderman, and Robert Oostenveld. "Localizing On-Scalp MEG Sensors Using an Array of Magnetic Dipole Coils." PLOS One 13, No. 5 (May 10, 2018): e0191111.

Vivaldi, Valentina, Sara Sommariva, and Alberto Sorrentino. "A Simplex Method for the Calibration of a MEG Device." Communications in Applied and Industrial Mathematics 10 (Jan. 1, 2019): 35-46.

Nagel, S., & Spüler, M. (2019). Asynchronous non-invasive high-speed BCI speller with robust non-control state detection. Scientific Reports, 9(1), 8269.

Thielen, J., van den Broek, P., Farquhar, J., & Desain, P. (2015). Broad-Band Visually Evoked Potentials: Re(con) volution in Brain-Computer Interfacing. PloS One, 10(7), e0133797. https://doi.org/10.1371/journal.pone.0133797.

J. Kitching, "Chip-scale atomic devices," Appl. Phys. Rev. 5(3), 031302 (2018), 39 pages.

Manon Kok, Jeroen D. Hol and Thomas B. Schon (2017), "Using Inertial Sensors for Position and Orientation Estimation", Foundations and Trends in Signal Processing: vol. 11: No. 1-2, pp. 1-153. http://dx.doi.org/10.1561/2000000094.

International Search Report and Written Opinion for PCT Application No. PCT/US20/22979 dated Jun. 26, 2020.

Allred, J. C., Lyman, R. N., Kornack, T. W., & Romalis, M. V. (2002). High-sensitivity atomic magnetometer unaffected by spin-exchange relaxation. Physical review letters, 89(13), 130801.

Balabas et al. Polarized alkali vapor with minute-long transverse spin-relaxation time, Phys. Rev. Lett. 105, 070801—Published Aug. 12, 2010.

Barbieri, F., Trauchessec, V., Caruso, L., Trejo-Rosillo, J., Telenczuk, B., Paul, E., . . . & Ouanounou, G. (2016). Local recording of

(56) References Cited

OTHER PUBLICATIONS biological magnetic fields using Giant Magneto Resistance-based micro-probes. Scientific reports, 6, 39330.

Dmitry Budker and Michael Romalis, "Optical Magnetometry," Nature Physics, 2008, https://arxiv.org/abs/physics/0611246v1.

Anthony P. Colombo, Tony R. Carter, Amir Borna, Yuan-Yu Jau, Cort N. Johnson, Amber L. Dagel, and Peter D. D. Schwindt, "Four-channel optically pumped atomic magnetometer for magnetoencephalography," Opt. Express 24, 15403-15416 (2016).

Dang, H.B. & Maloof, A.C. & Romalis, Michael. (2009). Ultra-high sensitivity magnetic field and magnetization measurements with an atomic magnetometer. Applied Physics Letters. 97. 10.1063/1. 3491215.

Donley, E.A. & Hodby, E & Hollberg. L & Kitching, J. (2007). Demonstration of high-performance compact magnetic shields for chip-scale atomic devices. The Review of scientific instruments. 78. 083102.

Hämäläinen, Matti & Hari, Riitta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol. 65, Issue 2. 413-497.

Hunter, D. and Piccolomo, S. and Pritchard, J. D. and Brockie, N. L. and Dyer, T. E. and Riis, E. (2018) Free-induction-decay magnetometer based on a microfabricated Cs vapor cell. Physical Review Applied (10).ISSN 2331-7019.

Jiménez-Martínez, R., Griffith, W. C., Wang, Y. J., Knappe, S., Kitching, J., Smith, K., & Prouty, M. D. (2010). Sensitivity comparison of Mx and frequency-modulated bell-bloom Cs magnetometers in a microfabricated cell. IEEE Transactions on Instrumentation and Measurement, 59(2), 372-378.

Kiwoong Kim, Samo Begus, Hui Xia, Seung-Kyun Lee, Vojko Jazbinsek, Zvonko Trontelj, Michael V. Romalis, Multi-channel atomic magnetometer for magnetoencephalography: A configuration study. NeuroImage 89 (2014) 143-151 http://physics.princeton.edu/romalis/papers/Klm_2014.pdf.

Knappe, Svenja & Sander, Tilmann & Trahms, Lutz. (2012). Optically-Pumped Magnetometers for MEG. Magnetoencephalography: From Signals to Dynamic Cortical Networks. 993-999. 10.1007/978-3-642-33045-2_49.

Kominis, I.K., Kornack, T.W., Allred, J.C. and Romalis, M.V., 2003. A subfemtotesla multichannel atomic magnetometer. Nature, 422(6932), p. 596.

Korth, H., K. Strohbehn, F. Tejada, A. G. Andreou, J. Kitching, S. Knappe, S. J. Lehtonen, S. M. London, and M. Kafel (2016), Miniature atomic scalarmagnetometer for space based on the rubidium isotope 87Rb, J. Geophys. Res. Space Physics, 121, 7870-7880, doi:10.1002/2016JA022389.

Lenz, J. and Edelstein, S., 2006. Magnetic sensors and their applications. IEEE Sensors journal, 6(3), pp. 631-649.

Li, S & Vachaspati, Pranjal & Sheng, Dehong & Dural, Nezih & Romalis, Michael. (2011). Optical rotation in excess of 100 rad generated by Rb vapor in a multipass cell. Phys. Rev. A. 84. 10.1103/PhysRevA.84.061403.

Maze, J. R., Stanwix, P. L., Hodges, J. S., Hong, S., Taylor, J. M., Cappellaro, P., . . . & Yacoby, A. (2008). Nanoscale magnetic sensing with an individual electronic spin in diamond. Nature, 455(7213), 644.

Sander TH, Preusser J, Mhaskar R, Kitching J, Trahms L, Knappe S. Magnetoencephalography with a chip-scale atomic magnetometer. Biomed Opt Express. 2012;3(5):981-90.

J. Seltzer, S & Romalis, Michael. (2010). High-temperature alkali vapor cells with antirelaxation surface coatings. Journal of Applied Physics. 106. 114905-114905. 10.1063/1.3236649.

Seltzer, S. J., and Romalis, M.V., "Unshielded three-axis vector operation of a spin-exchange-relaxation-free atomic magnetometer." Applied physics letters 85.20 (2004): 4804-4806.

Sheng, Dong & R. Perry, Abigail & Krzyzewski, Sean & Geller, Shawn & Kitching, John & Knappe, Svenja. (2017). A microfabricated optically-pumped magnetic gradiometer. Applied Physics Letters. 110. 10.1063/1.4974349.

Sheng, Dehong & Li, S & Dural, Nezih & Romalis, Michael. (2013). Subfemtotesla Scalar Atomic Magnetometry Using Multipass Cells. Physical review letters. 110. 160802. 10.1103/PhysRevLett. 110.160802.

Volkmar Schultze et al. An Optically Pumped Magnetometer Working in the Light-Shift Dispersed Mz Mode, Sensors 2017, 17, 561; doi:10.3390/s17030561.

Fang, J. and Qin, J., 2012. In situ triaxial magnetic field compensation for the spin-exchange-relaxation-free atomic magnetometer. Review of Scientific Instruments, 83(10), p. 103104.

Joon Lee, Hyun & Shim, Jeong & Moon, Han Seb & Kim, Kiwoong. (2014). Flat-response spin-exchange relaxation free atomic magnetometer under negative feedback. Optics Express. 22. 10.1364/OE.22.019887.

Griffith, Clark & Jimenez-Martinez, Ricardo & Shah, Vishal & Knappe, Svenja & Kitching, John. (2009). Miniature atomic magnetometer integrated with flux concentrators. Applied Physics Letters—Appl Phys Lett. 94. 10.1063/1.3056152.

Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.2885711.

Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-x.

Kim, Young Jin & Savukov, I. (2016). Ultra-sensitive Magnetic Microscopy with an Optically Pumped Magnetometer. Scientific Reports. 6. 24773. 10.1038/srep24773.

Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.

Orang Alem, Rahul Mhaskar, Ricardo Jiménez-Martínez, Dong Sheng, John LeBlanc, Lutz Trahms, Tilmann Sander, John Kitching, and Svenja Knappe, "Magnetic field imaging with microfabricated optically-pumped magnetometers," Opt. Express 25, 7849-7858 (2017).

Slocum et al., Self-Calibrating Vector Magnetometer for Space, https://esto.nasa.gov/conferences/estc-2002/Papers/B3P4(Slocum). pdf.

Dupont-Roc, J & Haroche, S & Cohen-Tannoudji, C. (1969). Detection of very weak magnetic fields (10-9gauss) by 87Rb zero-field level crossing resonances. Physics Letters A—Phys Lett A. 28. 638-639. 10.1016/0375-9601(69)90480-0.

J. A. Neuman, P. Wang, and A. Gallagher, Robust high-temperature sapphire cell for metal vapors, Review of Scientific Instruments, vol. 66, Issue 4, Apr. 1995, pp. 3021-3023.

Borna, Amir, et al. "A 20-channel magnetoencephalography system based on optically pumped magnetometers." Physics in Medicine & Biology 62.23 (2017): 8909.

R. E. Slocum & L. J. Ryan, Design and operation of the minature vector laser magnetometer, Nasa Earth Science Technology Conference 2003.

Schoenmaker, Jeroen & R Pirota, K & Teixeira, Julio. (2013). Magnetic flux amplification by Lenz lenses. The Review of scientific instruments. 84. 085120. 10.1063/1.4819234.

Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically pumped magnetometer. Applied Optics. 56. 5927. 10.1364/AO.56.005927.

Masuda, Y & Ino, T & Skoy, Vadim & Jones, G.L. (2005). 3He polarization via optical pumping in a birefringent cell. Applied Physics Letters. 87. 10.1063/1.2008370.

(56) References Cited

OTHER PUBLICATIONS

A.B. Baranga et al., An atomic magnetometer for brain activity imaging, Real Time Conference 2005. 14th IEEE-NPSS. pp. 417-418.
Larry J. Ryan, Robert E. Slocum, and Robert B. Steves, Miniature Vector Laser Magnetometer Measurements of Earth's Field, May 10, 2004, 4 pgs.
Lorenz, V. O., Dai, X., Green, H., Asnicar, T. R., & Cundiff, S. T. (2008). High-density, high-temperature alkali vapor cell. Review of Scientific Instruments, 79(12), 4 pages.
F. Jackson Kimball, D & Dudley, J & Li, Y & Thulasi, Swecha & Pustelny, Szymon & Budker, Dmitry & Zolotorev, Max. (2016). Magnetic shielding and exotic spin-dependent interactions. Physical Review D. 94. 10.1103/PhysRevD.94.082005.
Huang, Haichao, et al. "Single-beam three-axis atomic magnetometer." Applied Physics Letters 109.6 (2016): 062404. (Year: 2016).
Scott Jeffrey Seltzer: "Developments in alkali-metal atomic magnetometry", Nov. 1, 2008 (Nov. 1, 2008), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.
Haifeng Dong et al: "Atomic-Signal-Based Zero-Field Finding Technique for Unshielded Atomic Vector Magnetometer", IEEE Sensors Journal, IEEE Service Center, New York, NY, US, vol. 13, No. 1, Jan. 1, 2013 (Jan. 1, 2013), pp. 186-189.
Boto, E, Holmes, N, Leggett, J, Roberts, G, Shah, V, Meyer, SS, Muñoz, LD, Mulinger, KJ, Tierney, TM, Bestmann, S, Barnes, GR, Bowtell, R & Brookes, MJ 2018, 'Moving magnetoencephalography towards real world applications with a wearable system', Nature, vol. 555, pp. 657-661.
Ijsselsteijn, R & Kielpinski, Mark & Woetzel, S & Scholtes, Theo & Kessler, Ernst & Stolz, Ronny & Schultze, V & Meyer, H-G. (2012). A full optically operated magnetometer array: An experimental study. The Review of scientific instruments. 83. 113106. 10.1063/1.4766961.
Okada, Y.C., Lahteenmaki, A. and Xu, C., "Experimental analysis of distortion of magnetoencephalography signals by the skull." Clinical neurophysiology 110 (2), 230-238 (1999).
Robinson, J.T., Pohlmeyer, E., Gather, M.C., Kemere, C., Kitching, J.E., Malliaras, G.G., Marblestone, A., Shepard, K.L., Stieglitz, T. and Xie, C., "Developing Next-Generation Brain Sensing Technologies—A Review." IEEE sensors journal, 19(22), 10163-10175 (2019).
Shah, V., Knappe, S., Schwindt, P.D. and Kitching, J., "Subpicotesla atomic magnetometry with a microfabricated vapour cell." Nature Photon 1, 649-652 (2007).
Giffith, W.C., Knappe, S. and Kitching, J., "Femtotesla atomic magnetometry in a microfabricated vapor cell." Optics express 18, (26), 27167-27172 (2010).
Tierney, T.M., Holmes, N., Mellor, S., López, J.D., Roberts, G., Hill, R.M., Boto, E., Leggett, J., Shah, V., Brookes, M.J. and Bowtell, R., "Optically pumped magnetometers: From quantum origins to multichannel magnetoencephalography." NeuroImage, 199, 598-608 (2019).
Iivanainen, J., Zetter, R., Grön, M., Hakkarainen, K. and Parkkonen, L., "On-scalp MEG system utilizing an actively shielded array of optically-pumped magnetometers." Neuroimage 194, 244-258 (2019).
Iivanainen, J., Stenroos, M. and Parkkonen, L., "Measuring MEG closer to the brain: Performance of on-scalp sensor arrays." NeuroImage 147, 542-553 (2017).
Kitching, J., Knappe, S., Gerginov, V., Shah, V., Schwindt, P.D., Lindseth, B., Donley E.A., "Chip-scale atomic devices: precision atomic instruments based on MEMS." In Frequency Standards And Metrology, 445-453 (2009).
Kitching, J., Knappe, S. and Donley, E.A., "Atomic sensors—a review." IEEE Sensors Journal, 11(9), 1749-1758 (2011).
Budker, D. and Romalis, M., "Optical magnetometry". Nature physics, 3(4), 227-234 (2007).
Happer, W., "Optical pumping", Rev. Mod. Phys., 44 (2), 169-249 (1972).
Purcell, E.M., Field, G.B., "Influence of collisions upon population of hyperfine states in hydrogen", Astrophys. J., 124, 542 (1956).
Ledbetter, M.P., Savukov, I.M., Acosta, V.M., Budker, D. and Romalis, M.V., "Spin-exchange-relaxation-free magnetometry with Cs vapor." Physical Review A, 77(3), 033408 (2008).
Bloom, A. L., "Principles of operation of the rubidium vapor magnetometer." Applied Optics 1(1), 61-68 (1962).
Bell, W.E., and Bloom, A.L., "Optically driven spin precession." Physical Review Letters 6, (6), 280 (1961).
Roberts, G., Holmes, N., Alexander, N., Boto, E., Leggett, J., Hill, R.M., Shah, V., Rea, M., Vaughan, R., Maguire, E.A. and Kessler, K., "Towards OPM-MEG in a virtual reality environment" NeuroImage, 199, 408-417 (2019).
Zhang, R., Xiao, W., Ding, Y., Feng, Y., Peng, X., Shen, L., Sun, C., Wu, T., Wu, Y., Yang, Y. and Zheng, Z., "Recording brain activities in unshielded Earth's field with optically pumped atomic magnetometers." Science Advances, 6(24) (2020).
De Cheveigné, A., Wong, D.D., Di Liberto, G.M., Hjortkjaer, J., Slaney, M. and Lalor, E., "Decoding the auditory brain with canonical component analysis." NeuroImage, 172, 206-216 (2018).
Mellinger, J., Schalk, G., Braun, C., Preissl, H., Rosenstiel, W., Birbaumer, N. and Kubler, A., "An MEG-based brain-computer interface (BCI) " Neuroimage, 36(3), 581-593 (2007).
Wolpaw, J.R., McFarland, D.J., Neat, G.W. and Forneris, C.A., "An EEG-based brain-computer interface for cursor control." Electroencephalography and clinical neurophysiology, 78(3), 252-259 (1991).
Lightfoot, G., "Summary of the N1-P2 cortical auditory evoked potential to estimate the auditory threshold in adults". Seminars in hearing, 37(1), 1 (2016).
Virtanen, J., Ahveninen, J., Ilmoniemi, R. J., Näätänen, R., & Pekkonen, E., "Replicability of MEG and EEG measures of the auditory N1/N1m-response." Electroencephalography and Clinical Neurophysiology/Evoked Potentials Section, 108(3), 291-298(1998).
Gascoyne, L., Furlong, P. L., Hillebrand, A., Worthen, S. F., & Witton, C., "Localising the auditory N1m with event-related beamformers: localisation accuracy following bilateral and unilateral stimulation." Scientific reports, 6(1), 1-9 (2016).
Borna, A., Carter, T.R., Goldberg, J.D., Colombo, A.P., Jau, Y.Y., Berry, C., McKay, J., Stephen, J., Weisend, M. and Schwindt, P.D., "A 20-channel magnetoencephalography system based on optically pumped magnetometers." Physics in Medicine & Biology, 62(23), 8909 (2017).
Pyragius, T., Marin Florez, H., & Fernholz, T. (2019). A Voigt effect based 3D vector magnetometer. Physical Review A, 100(2), https://doi.org/10.1103/PhysRevA.100.023416.
Rui Zhang, Rahul Mhaskar, Ken Smith, Easswar Balasubramaniam, Mark Prouty. "All Optical Scalar Atomic Magnetometer Capable of Vector Measurement," Submitted on Nov. 17, 2020. https://arxiv.org/abs/2011.08943; Geometries, Inc., San Jose, CA, 95131, USA.

* cited by examiner

INTEGRATED MAGNETOMETER ARRAYS FOR MAGNETOENCEPHALOGRAPHY (MEG) DETECTION SYSTEMS AND METHODS

CROSS-REFERENCE TO RELATED APPLICATIONS

This application claims the benefit of U.S. Provisional Patent Application Ser. Nos. 62/826,045, filed Mar. 29, 2019, and 62/858,636, filed Jun. 7, 2019, both of which are incorporated herein by reference in their entireties.

FIELD

The present disclosure is directed to the area of magnetic field measurement systems using an array of optically pumped magnetometers (OPMs). The present disclosure is also directed to magnetic field measurement systems and methods for high spatial resolution magnetoencephalography (MEG).

BACKGROUND

In the nervous system, neurons propagate signals via action potentials. These are brief electric currents which flow down the length of a neuron causing chemical transmitters to be released at a synapse. The time-varying electrical currents within an ensemble of neurons generates a magnetic field. Magnetoencephalography (MEG), the measurement of magnetic fields generated by the brain, is one method for observing these neural signals.

Existing systems for observing or measuring MEG typically utilize superconducting quantum interference devices (SQUIDs) or collections of discrete optically pumped magnetometers (OPMs). SQUIDs require cryogenic cooling which is bulky and expensive and requires a lot of maintenance which preclude their use in mobile or wearable devices. Many conventional applications of optically pumped magnetometers to MEG involve a single vapor cell inside a 1 to 2 cm package, preventing or hindering spatial resolution beyond this range. Thermal management and magnetic cross talk also pose other practical limitations to achieving high spatial resolution with discrete magnetometers.

BRIEF SUMMARY

One embodiment is an array of optically pumped magnetometers that includes a vapor cell arrangement having a wafer defining one or more cavities and alkali metal atoms disposed in the cavities to provide an alkali metal vapor; an array of light sources, each of the light sources arranged to illuminate a different portion of the one or more cavities of the vapor cell arrangement with light; at least one mirror arranged to reflect the light from the array of light sources after the light passes through the one or more cavities of the vapor cell arrangement; and an array of detectors to receive light reflected by the at least one mirror, wherein each of the detectors is arranged to receive light originating from one of the light sources.

In at least some embodiments, the array of optically pumped magnetometers further includes an array of microlenses disposed between the light sources and the vapor cell arrangement. In at least some embodiments, the light sources and detectors are arranged in a plurality of pairs, each pair including one of the light sources and one of the detectors, wherein, for each of the pairs, the light source and the detector are positioned opposite each other relative to an optical axis of a one of the microlenses that is arranged to receive light from the light source. In at least some embodiments, the microlenses are configured to receive light from the light sources. In at least some embodiments, the microlenses are further configured to receive light reflected by the at least one mirror and to direct the reflected light to the detectors.

In at least some embodiments, the array of optically pumped magnetometers further includes at least one quarter-wave plate disposed between the light sources and the vapor cell arrangement to receive the light from the light sources prior to entry into the one or more cavities. In at least some embodiments, the array of optically pumped magnetometers further includes an array of polarizing beamsplitters disposed between the light sources and the vapor cell arrangement and configured to direct light from the light sources to the vapor cell arrangement and to direct light reflected by the at least one mirror to the detectors.

In at least some embodiments, the array of optically pumped magnetometers further includes a magnetic field generator disposed adjacent the vapor cell arrangement to generate a magnetic field within the one or more cavities. In at least some embodiments, magnetic field generator is configured to independently generate magnetic fields in two orthogonal directions.

In at least some embodiments, the at least one mirror is disposed within the one or more cavities. In at least some embodiments, the at least one mirror is disposed outside of the one or more cavities. In at least some embodiments, the one or more cavities is a plurality of cavities with each of the light sources arranged to illuminate a different one of the cavities. In at least some embodiments, the one or more cavities is a single cavity.

In at least some embodiments, the array of optically pumped magnetometers further includes a substrate, wherein the light sources and the detectors are all disposed on the substrate. In at least some embodiments, the array of optically pumped magnetometers is a two-dimensional array. In at least some embodiments, the array of optically pumped magnetometers is a one-dimensional linear array.

In at least some embodiments, the array of optically pumped magnetometers further includes a plurality of turning mirrors disposed between the light sources and the vapor cell arrangement to direct light from the light sources to the vapor cell arrangement. In at least some embodiments, the at least one mirror is a plurality of retroreflective mirrors.

Another embodiment is a magnetic field measurement system that includes any of the arrays of optically pumped magnetometers described above and a computing device configured to receive signals from the detectors of the array.

A further embodiment is a method of measuring a magnetic field that includes providing any of the arrays of optically pumped magnetometers describe above; illuminating the vapor cell arrangement using the light sources; in response to the illuminating, receiving signals from the detectors; and measuring the magnetic field using the signals.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1A:
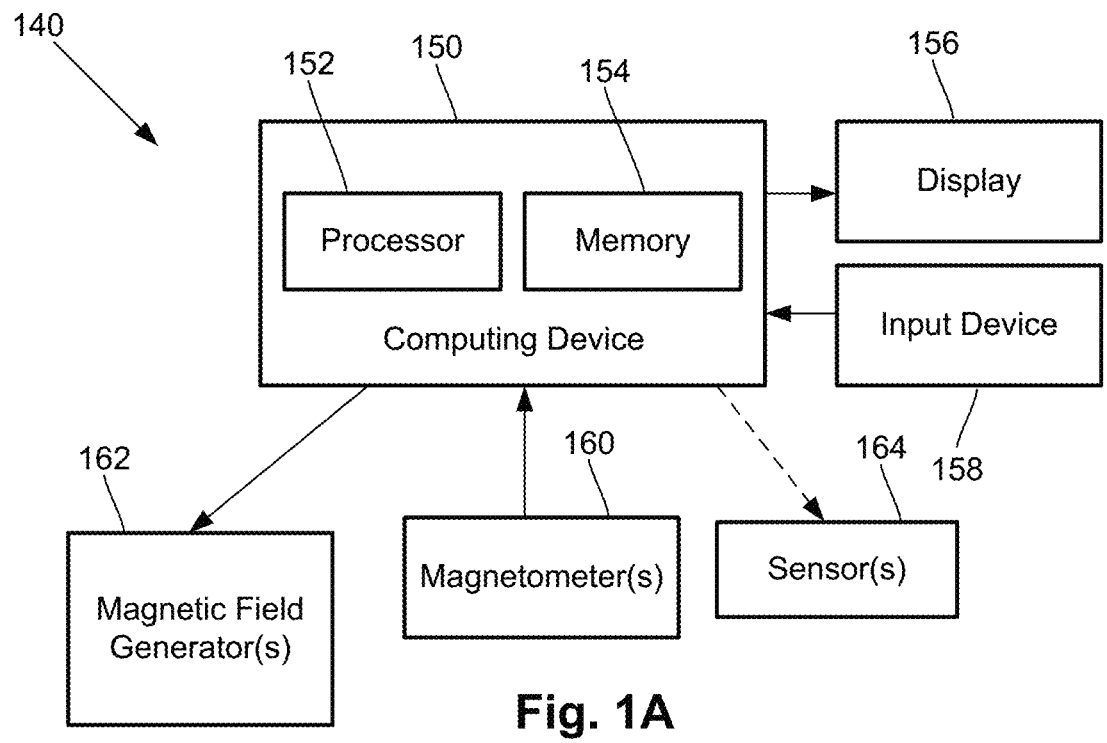
FIG. 1A is a schematic block diagram of one embodiment of a magnetic field measurement system, according to the invention.

The present disclosure is directed to the area of magnetic field measurement systems using an array of optically pumped magnetometers (OPMs). The present disclosure is also directed to magnetic field measurement systems and methods for high spatial resolution magnetoencephalography (MEG). Although the present disclosure utilizes MEG to exemplify the arrays, systems, and methods described herein, it will be understood that the arrays, systems, and methods can be used in any other suitable application.

Herein the terms "ambient background magnetic field" and "background magnetic field" are interchangeable and used to identify the magnetic field or fields associated with sources other than the magnetic field measurement system and the biological source(s) (for example, neural signals from a user's brain) or other source(s) of interest. The terms can include, for example, the Earth's magnetic field, as well as magnetic fields from magnets, electromagnets, electrical devices, and other signal or field generators in the environment, except for the magnetic field generator(s) that are part of the magnetic field measurement system.

The terms "gas cell", "vapor cell", and "vapor gas cell" are used interchangeably herein. Below, a gas cell containing alkali metal vapor is described, but it will be recognized that other gas cells can contain different gases or vapors for operation.

An optically pumped magnetometer (OPM) is a basic component used in optical magnetometry to measure magnetic fields. While there are many types of OPMs, in general magnetometers operate in two modalities: vector mode and scalar mode. In vector mode, the OPM can measure one, two, or all three vector components of the magnetic field; while in scalar mode the OPM can measure the total magnitude of the magnetic field.

Vector mode magnetometers measure a specific component of the magnetic field, such as the radial and tangential components of magnetic fields with respect to the scalp of the human head. Vector mode OPMs often operate at zero-field and may utilize a spin exchange relaxation free (SERF) mode to reach femto-Tesla sensitivities. A SERF mode OPM is one example of a vector mode OPM, but other vector mode OPMs can be used at higher magnetic fields. These SERF mode magnetometers can have high sensitivity but may not function in the presence of magnetic fields higher than the linewidth of the magnetic resonance of the atoms of about 10 nT, which is much smaller than the magnetic field strength generated by the Earth. As a result, conventional SERF mode magnetometers often operate inside magnetically shielded rooms that isolate the sensor from ambient magnetic fields including Earth's magnetic field.

Magnetometers operating in the scalar mode can measure the total magnitude of the magnetic field. (Magnetometers in the vector mode can also be used for magnitude measurements.) Scalar mode OPMs often have lower sensitivity than SERF mode OPMs and are capable of operating in higher magnetic field environments.

The magnetic field measurement systems described herein can be used to measure or observe electromagnetic signals generated by one or more sources (for example, neural signals or other biological sources). The system can measure biologically generated magnetic fields and, at least in some embodiments, can measure biologically generated magnetic fields in an unshielded or partially shielded environment. Aspects of a magnetic field measurement system will be exemplified below using magnetic signals from the brain of a user; however, biological signals from other areas of the body, as well as non-biological signals, can be measured using the system. In at least some embodiments, the system can be a wearable MEG system that can be used outside a magnetically shielded room. In at least some embodiments, the system can be a wearable MEG system that can be used in a magnetically shielded room with small compensation coils around the OPM, such as described, for example, in magnetic field measurement systems or methods described in U.S. Provisional Patent Application Ser. No. 62/983,406, incorporated herein by reference in its entirety.

FIG. 1A is a block diagram of components of one embodiment of a magnetic field measurement system 140. The system 140 can include a computing device 150 or any other similar device that includes a processor 152 and a memory 154, a display 156, an input device 158, one or more magnetometers 160 (for example, an array of magnetometers) which can be OPMs, one or more magnetic field generators 162, and, optionally, one or more sensors 164. The system 140 and its use and operation will be described herein with respect to the measurement of neural signals arising from signal sources in the brain of a user as an example. It will be understood, however, that the system can be adapted and used to measure other neural signals, other biological signals, as well as non-biological signals.

The computing device 150 can be a computer, tablet, mobile device, field programmable gate array (FPGA), microcontroller, or any other suitable device for processing information or instructions. The computing device 150 can be local to the user or can include components that are non-local to the user including one or both of the processor 152 or memory 154 (or portions thereof). For example, in at least some embodiments, the user may operate a terminal that is connected to a non-local computing device. In other embodiments, the memory 154 can be non-local to the user.

The computing device 150 can utilize any suitable processor 152 including one or more hardware processors that may be local to the user or non-local to the user or other components of the computing device. The processor 152 is configured to execute instructions, as described below.

Any suitable memory 154 can be used for the computing device 150. The memory 154 illustrates a type of computer-readable media, namely computer-readable storage media. Computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 156 can be any suitable display device, such as a monitor, screen, or the like, and can include a printer. In some embodiments, the display is optional. In some embodiments, the display 156 may be integrated into a single unit with the computing device 150, such as a tablet, smart phone, or smart watch. In at least some embodiments, the display is not local to the user. The input device 158 can be, for example, a keyboard, mouse, touch screen, track ball, joystick, voice recognition system, or any combination thereof, or the like. In at least some embodiments, the input device is not local to the user.

The magnetic field generator(s) 162 can be, for example, Helmholtz coils, solenoid coils, planar coils, saddle coils, electromagnets, permanent magnets, or any other suitable arrangement for generating a magnetic field. As an example, the magnetic field generator 162 can include three orthogonal sets of coils to generate magnetic fields along three orthogonal axes. Other coil arrangements can also be used. The optional sensor(s) 164 can include, but are not limited to, one or more magnetic field sensors, position sensors, orientation sensors, accelerometers, image recorders, or the like or any combination thereof.

The one or more magnetometers 160 can be any suitable magnetometer including, but not limited to, any suitable optically pumped magnetometer. Arrays of magnetometers are described in more detail herein. In at least some embodiments, at least one of the one or more magnetometers (or all of the magnetometers) of the system is arranged for operation in the SERF mode. Examples of magnetic field measurement systems or methods of making such systems or components for such systems are described in U.S. Patent Application Publications Nos. US 2020/0072916; US 2020/0056263; US 2020/0025844; US 2020/0057116; US 2019/0391213; and US 2020/0057115; U.S. patent application Ser. Nos. 16/456,975; 16/573,394; 16/573,524; 16/679,048; 16/741,593; and Ser. No. 16/752,393, and U.S. Provisional Patent Application Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032; 62/926,043; 62/933,085; 62/960,548; 62/971,132; and 62/983,406, all of which are incorporated herein by reference in their entireties.

Figure 1B:
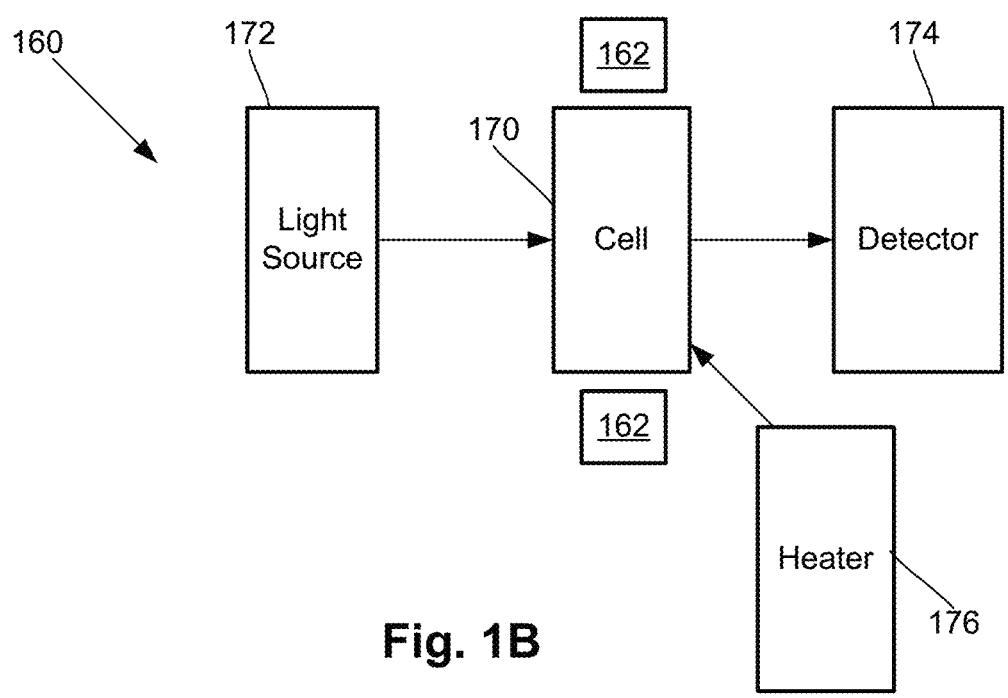
FIG. 1B is a schematic block diagram of one embodiment of a magnetometer, according to the invention.

FIG. 1B is a schematic block diagram of one embodiment of a magnetometer 160 which includes an alkali metal gas cell 170 (also referred to as a "cell" or "vapor cell"); a heating device 176 to heat the cell 170; a light source 172; and a detector 174. In addition, coils of a magnetic field generator 162 can be positioned around the cell 170. The gas cell 170 can include, for example, an alkali metal vapor (for example, rubidium in natural abundance, isotopically enriched rubidium, potassium, or cesium, or any other suitable alkali metal such as lithium, sodium, or francium) and, optionally, one, or both, of a quenching gas (for example, nitrogen) or a buffer gas (for example, nitrogen, helium, neon, or argon). In some embodiments, the vapor cell may include the alkali metal atoms in a prevaporized form prior to heating to generate the vapor.

The light source 172 can include, for example, a laser to, respectively, optically pump the alkali metal atoms and to probe the vapor cell. The light source 172 may also include optics (such as lenses, waveplates, collimators, polarizers, and objects with reflective surfaces) for beam shaping and polarization control and for directing the light from the light source to the cell and detector. Examples of suitable light sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source. In some embodiments, the light source 172 may include two light sources: a pump light source and a probe light source.

The detector 174 can include, for example, an optical detector to measure the optical properties of the transmitted light field amplitude, phase, or polarization, as quantified through optical absorption and dispersion curves, spectrum, or polarization or the like or any combination thereof. Examples of suitable detectors include, but are not limited to, a photodiode, charge coupled device (CCD) array, CMOS array, camera, photodiode array, single photon avalanche diode (SPAD) array, avalanche photodiode (APD) array, or any other suitable optical sensor array that can measure the change in transmitted light at the optical wavelengths of interest.

Figure 2:
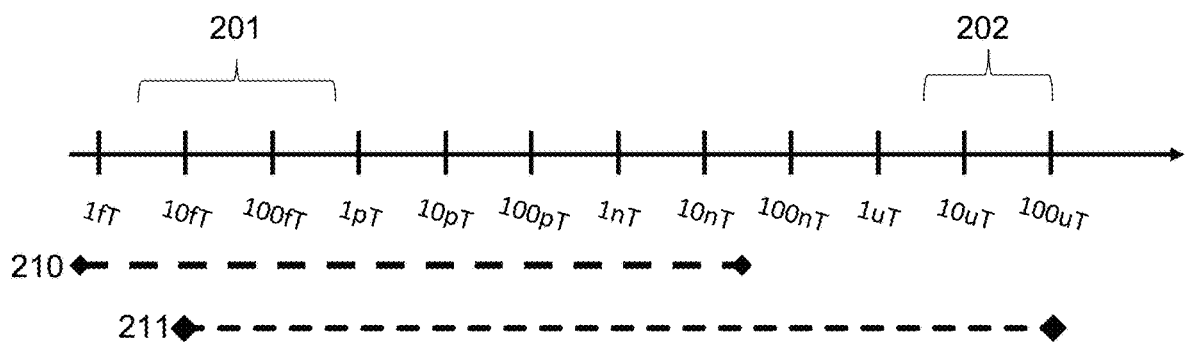
FIG. 2 shows a magnetic spectrum with lines indicating dynamic ranges of magnetometers operating in different modes.

FIG. 2 shows the magnetic spectrum from 1 fT to 100 µT in magnetic field strength on a logarithmic scale. The magnitude of magnetic fields generated by the human brain are indicated by range 201 and the magnitude of the background ambient magnetic field, including the Earth's magnetic field, by range 202. The strength of the Earth's magnetic field covers a range as it depends on the position on the Earth as well as the materials of the surrounding environment where the magnetic field is measured. Range 210 indicates the approximate measurement range of a magnetometer (e.g., an OPM) operating in the SERF mode (e.g., a SERF magnetometer) and range 211 indicates the approximate measurement range of a magnetometer operating in a scalar mode (e.g., a scalar magnetometer.) Typically, a SERF magnetometer is more sensitive than a scalar magnetometer, but many conventional SERF magnetometers typically only operate up to about 0 to 200 nT while the scalar magnetometer starts in the 10 to 100 fT range but extends above 10 to 100 µT.

As presented herein, the spatial resolution of a magnetic field measurement system can be increased through design and manufacture of an integrated array of OPMs. In at least some embodiments, microfabrication techniques can be used to generate arrays of lenses, light sources, detectors, and vapor cells.

Figure 3A:
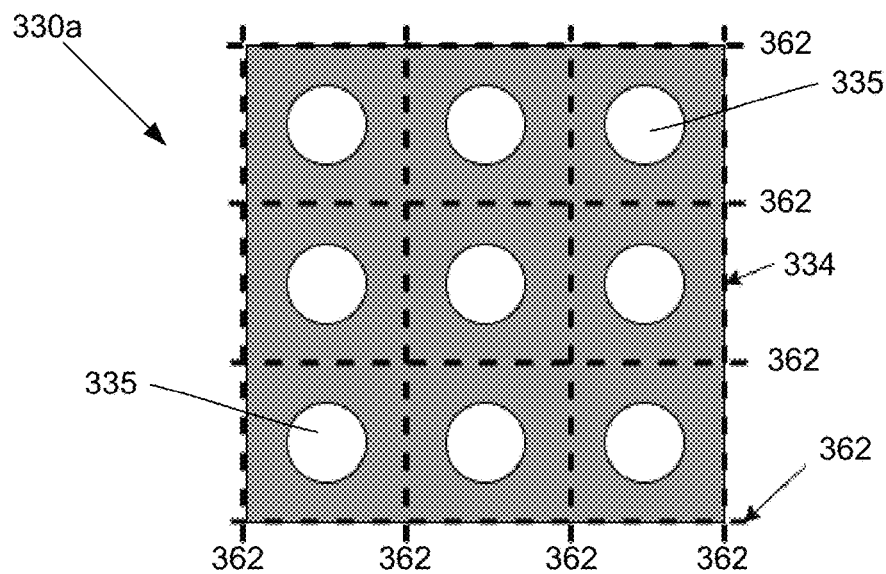
FIGS. 3A and 3B are, respectively, a top view of a wafer of one embodiment of an array of optically pumped magnetometers and a side view of the array of optically pumped magnetometers, according to the invention.
Figure 3B:
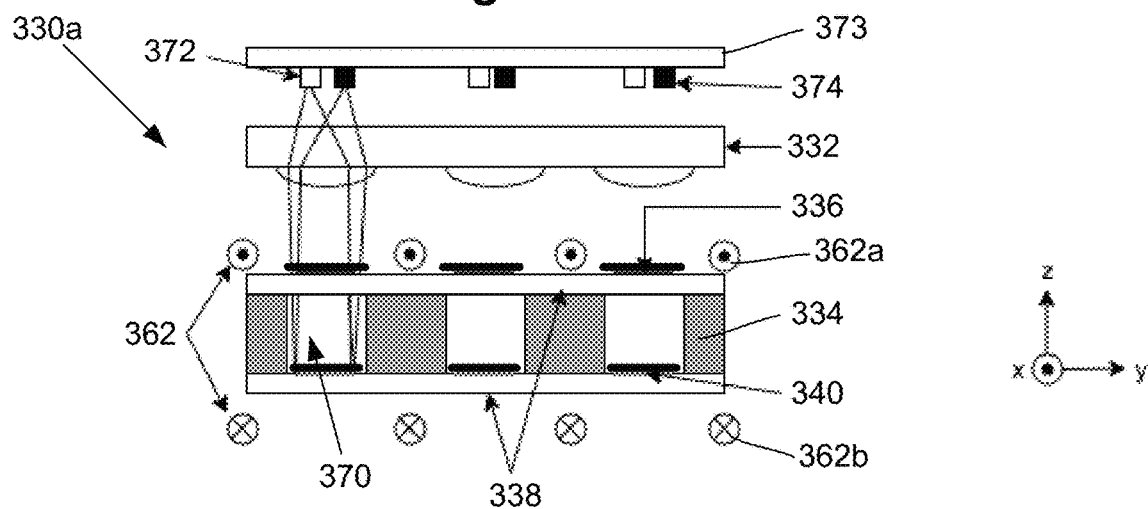

FIGS. 3A and 3B illustrate one embodiment of an integrated OPM array 330a that, at least in some embodiments, is suitable for high resolution MEG and other applications. FIG. 3A illustrates a top view of a wafer 334 (for example, a wafer of silicon, silicon dioxide, or any other suitable material) with an array of cavities 335 for vapor cells. The array of cavities 335 can be formed by any suitable technique including, but not limited to, photolithographic techniques. In the illustrated embodiment, the cavities 335 are formed in a 3×3 array. It will be understood that an array of any other suitable size can be used and that the array can be square, rectangular, octagonal, hexagonal, circular, or any other suitable shape. In the illustrated embodiment, the cavities 335 are arranged in a regular pattern with rows and columns. In other embodiments, any other regular pattern or any other regular or irregular arrangement of cavities 335 can be used. In the illustrated embodiments, the cavities 335 have a circular cross-section. In other embodiments, the cross-section can be square, rectangular, hexagonal, octagonal, oval, or any other regular or irregular shape and may be the same for all cavities or may be different for one or more cavities.

The spacing of the cavities 335 (for example, the center-to-center spacing) can be the same or different between adjacent cavities and the spacing along the rows can be the same or different from the spacing along the columns. In one embodiment, the center-to-center spacing of the cavities 335 is in the range of 3 to 20 mm or in the range of 4 to 10 mm or 4, 5, 6, 7, or 8 mm. The wafer 334 and cavities 335 can have any suitable thickness. In at least some embodiments, the wafer 334 and the cavities 335 have a thickness in a range of 1 to 10 mm or in a range or 2 to 8 mm or 2, 3, 4, 5, or 6 mm, although thinner or thicker wafers/cavities can also be used.

FIG. 3B is a side view of the OPM array 330a illustrating that the cavities in the wafer 334 are enclosed by two sealing layers 338. As an example, the sealing layers 338 can be made of glass (for example, Pyrex™) which may be anodically bonded or otherwise attached to the wafer 334. The sealing layer 338 between the cavities 335 and the light sources 372 is substantially transparent to the light emitted by the light sources 372. The sealing layers 338 can each be a single piece that covers all of the cavities 335 or may be formed of two or more individual pieces that each cover one or more of the cavities.

The wafer 334 and sealing layers 338 form an array of vapor cells 370. Each of the vapor cells 370 contains an alkali metal vapor (for example, potassium, rubidium, or cesium) in the cavities 335 and may also contain a buffer gas (for example, nitrogen, neon, or argon), quenching gas, or the like. In some embodiments, the vapor cell 370 may include the alkali metal atoms in a prevaporized form prior to heating to generate the vapor.

The OPM array 330a also includes an array of light sources 372. In at least some embodiments, the array of light sources 372 includes one light source per vapor cell 370, as illustrated in FIG. 3B. In at least some embodiments, the light sources 372 are Vertical Cavity Surface Emitting Lasers (VCSELs), although any other suitable light source, such as a light-emitting diode (LED), organic light-emitting diode (OLED), or any other suitable type of laser can also be used. The light sources 372 can be disposed on a substrate 373 and, at least in some embodiments, may be formed on the substrate using, for example, microfabrication techniques.

The light from the light sources 372 is expanded by an array of microlenses 332 and passes through a set of quarter-wave plates 336 before entering the vapor cells 370. The microlenses 332 can be individual lenses or can be formed in a connected array of microlenses, as illustrated in FIG. 3B. The quarter-wave plates 336 can be formed or patterned on one of the sealing layers 338, as illustrated in FIG. 3B, or can be separate discrete components. The quarter-wave plates 336 can be individual plates, as illustrated in FIG. 3B, that are each associated with a single vapor cell 370 or can be one or more plates that cover multiple vapor cells (or even all of the vapor cells.) In at least some embodiments, the quarter-wave plates 336 can be made by microfabrication techniques.

After passing through the vapor cells 370, mirrors 340 reflect the light back through the vapor cells again. The mirrors 340 can be formed on one of the sealing layers 338, as illustrated in FIG. 3B, or can be separate discrete components. In at least some embodiments, the mirrors 340 are disposed in the vapor cell 370 to reduce the number of air/solid interfaces that the light passes through. In other embodiments, the mirrors 340 can be positioned on the opposite side of the sealing layer 338 from that illustrated in FIG. 3B or can be spaced apart from the sealing layer 338 as independent elements (see, for example, FIGS. 4B, 5B, 6B, and 7B.) Inclusion of the mirrors 370, such as retro-reflecting mirrors, eliminates the positioning of detectors 374 on the opposite side of the vapor cells 370 from the light sources 372 which can reduce the distance from the active part of the OPM (e.g., the alkali metal vapor cell) to the magnetic field source inside the skull. In at least some embodiments, the double pass of the light through the vapor cell 370 (i.e., first pass prior to reflection by the mirror 340 and second pass after reflection) can permit operation of the vapor cell at a lower temperature than would be possible with single pass operation due to higher optical depth. In at least some embodiments, the mirrors 340 can be made by microfabrication techniques.

The light reflected by the mirrors 340 passes through the vapor cells 370 and microlenses 332 towards an array of detectors 374 (for example, photodiodes). In at least some embodiments, the detectors 374 are mounted in close proximity to the light sources 372 as illustrated in FIG. 3B. In at least some embodiments, for each member of the OPM array 330a, the light source 372 and the detector 374 are mounted in opposite directions off of the optical axis of the microlens 332, so that light from the light source 372 can be collected by the detector 374. In at least some embodiments, the detectors 374 can be disposed on the same substrate 373 as the light sources or can be disposed on a different substrate. In at least some embodiments, the detectors 374 may be formed on the substrate using microfabrication techniques.

A magnetic field generator 362 is arranged around the vapor cells 370 to generate magnetic fields in the x or y directions, transverse to the z input axis. As illustrated in FIG. 3B, there is one set of coils 362*a* for the x-direction and one set of coils 362*b* for the y-direction. In some embodiments, the coils are arranged to be disposed between adjacent vapor cells 370/cavities 335, as illustrated in FIGS. 3A and 3B. In some embodiments, one set of coils 362*a* may be disposed on one side of the vapor cells and another set of coils 362*b* disposed on the other side of the vapor cells. In other embodiments, there may be coils from both sets 362*a*, 362*b* disposed on both sides of the vapor cells. In at least some embodiments, a single magnetic field coil can generate the modulation to drive a number of independent OPMs. In at least some embodiments, the geometry of the OPM array is such that relatively small compact coils can generate a uniform magnetic field across the entire array of vapor cells 370.

In at least some embodiments, an OPM array results in increased spatial resolution of the MEG system. An OPM array can include one or more features that can facilitate the increased spatial resolution such as, for example, the positioning of the light sources 372 and detectors 374 on the same side of the vapor cells 370, the formation of vapor cells in a silicon wafer, the use of microfabrication techniques to generate arrays of one or more of the following: microlenses 332, light sources 372 (such as VCSELs), detectors 374 (such as photodiodes), the alkali metal vapor cell 370, or other components of the OPM array 330*a*.

As an example of one embodiment of operation of the OPM array, if all other magnetic fields are zero, circularly polarized light generates atomic spin polarization of the alkali metal atoms in the vapor cell along the direction of light propagation. A small oscillating magnetic field in the x (or y) directions is generated by the magnetic field generator 362. This modulates the intensity of the light detected by the detectors 374. The signal at the first harmonic of the modulation frequency is linear in a small magnetic field (for example, a neural signal originating in the brain) of interest in the x (or y) direction, providing a measurement of the magnetic field of interest.

In at least some embodiments, the OPM array preferably operates when all fields are very near zero (for example, no more than about 100 nT). In this case, the OPMs operate in the spin-exchange relaxation-free (SERF) regime. In finite magnetic fields (e.g. the Earth's magnetic field), the system can operate in closed loop mode, where feedback from one of the OPMs or another sensor (operating as a reference) is used to zero the magnetic field at the reference. Other OPMs in the array measure small magnetic field deviations due to local sources (for example, neural signals in the brain) with respect to the reference OPM.

In at least some embodiments of a magnetic field measurement system, the system includes one OPM array, or multiple OPM arrays, disposed over a desired measurement surface (for example, in a helmet fitted to conform to a user's head for non-invasive measurement of neural signals in the brain.) Examples of non-invasive magnetic field measurement applications, systems, and methods are described in U.S. patent application Ser. No. 16/364,338 and U.S. Provisional Patent Application Ser. No. 62/829,124 and other references cited herein, all of which are incorporated herein by reference.

Figure 4A:
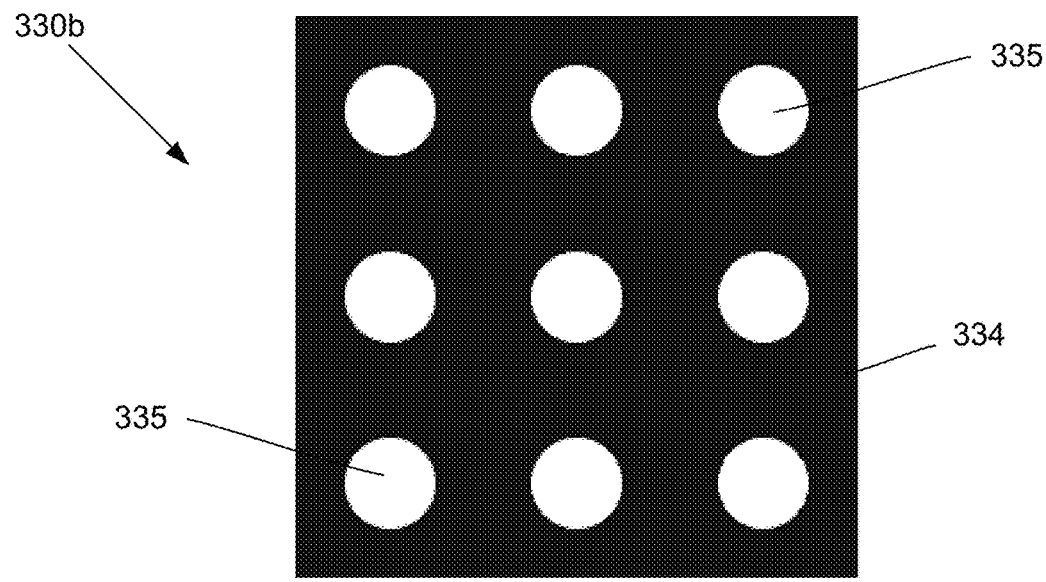
FIGS. 4A and 4B are, respectively, a top view of a wafer of another embodiment of an array of optically pumped magnetometers and a side view of the array of optically pumped magnetometers, according to the invention.
Figure 4B:
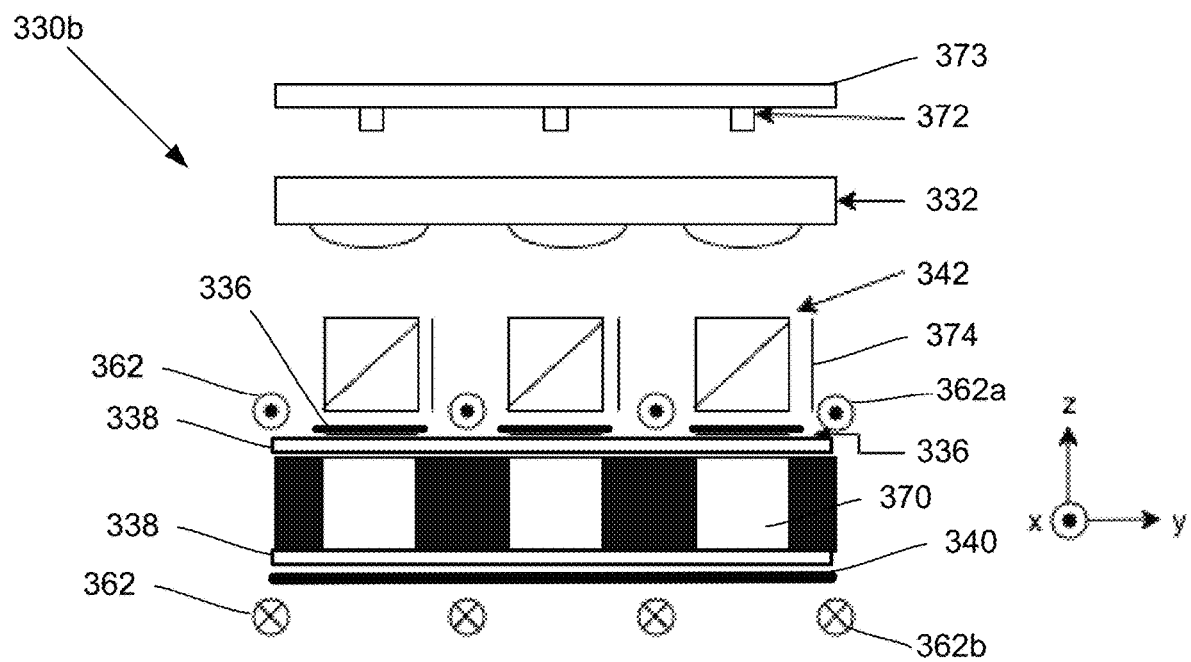

FIGS. 4A and 4B illustrate, respectively, a top view of another embodiment of the wafer 334 and a side view of another embodiment of an OPM array 330*b* that includes the light sources 372, microlenses 332, vapor cells 370, quarter-wave plates 336, mirrors 340, magnetic field generator 362, and detectors 374 as described above. However, in the embodiment illustrated in FIGS. 4A and 4B polarizing beamsplitters 342 are positioned between the microlenses 332 and the quarter-wave plates 336 and the detectors 374 are positioned to receive light from the polarizing beamsplitters 342. Optionally, the microlenses 332 are only disposed to receive light from the light source 372 and the light source may be aligned with the optical axis of the microlenses.

In this embodiment, the light sources 372 generate linearly polarized light (or a linear polarizer is positioned between the light source 372 and the polarizing beamsplitter 342) with the polarizing beamsplitters 342 arranged to allow the light to pass through the polarizing beamsplitters. After two passes through the quarter-wave plates 336 and vapor cells 370, the polarization of the light is changed so that the polarizing beamsplitters 342 reflect the light toward the detectors 374. Otherwise, the embodiment of FIGS. 4A and 4B is the same as the embodiment of FIGS. 3A and 3B and all of the design options and microfabrication techniques are the same for both embodiments.

Figure 5A:
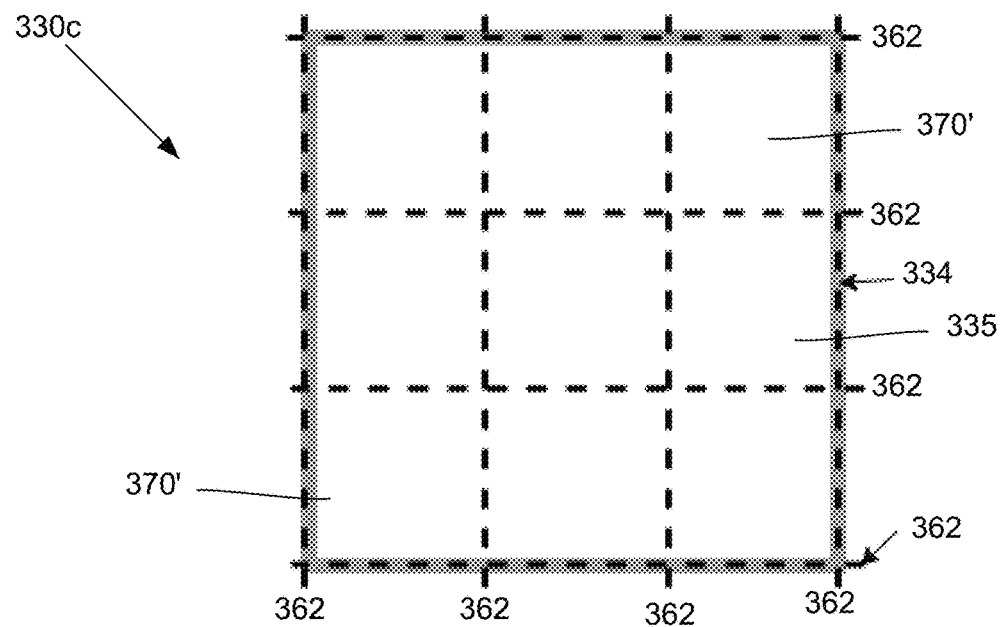
FIGS. 5A and 5B are, respectively, a top view of a wafer of a third embodiment of an array of optically pumped magnetometers and a side view of the array of optically pumped magnetometers, according to the invention.
Figure 5B:
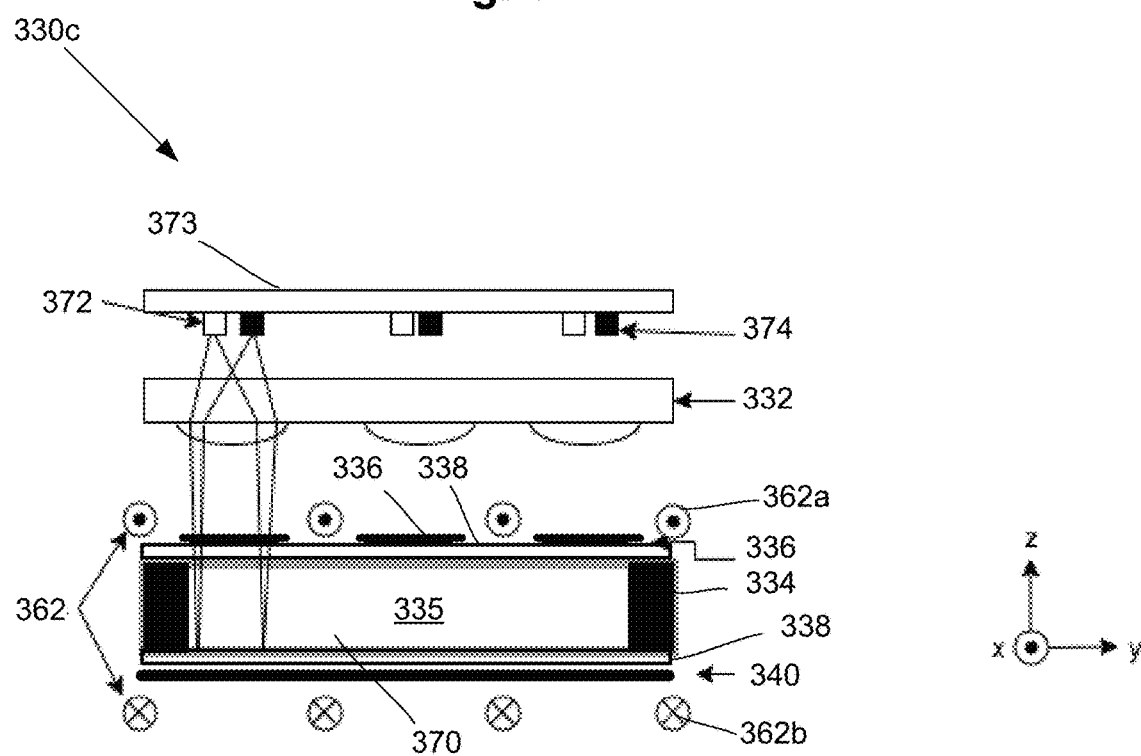

FIGS. 5A and 5B illustrate, respectively, a top view of another embodiment of the wafer 334 and a side view of another embodiment of an OPM array 330*c* that is the same as the embodiment of FIGS. 3A and 3B except that there is a single, larger cavity 335 rather than many smaller cavities. Although there is only a single cavity 335, there is still effectively multiple vapor cells as the presence of a buffer gas suppresses diffusion of alkali metal atoms between different regions 370' traversed by the light beams from different light sources. Thus, each of these regions 370' act as an individual vapor cell and permits making independent measurements. Otherwise, the embodiment of FIGS. 5A and 5B is the same as the embodiment of FIGS. 3A and 3B and all of the design options and microfabrication techniques are the same for both embodiments.

This configuration may be advantageous as there is a common vapor environment (same alkali metal vapor density, same buffer gas pressure) among the different illuminated regions 370'. It will be understood that, instead of a single large cavity, there can be multiple cavities that each contain two or more regions 370', which act as individual vapor cells, associated with different light sources. Moreover, any combination of cavities with a single region and cavities with multiple regions can be utilized.

The OPMs described herein can be sensitive to fields oriented transverse to the light as it propagates through the vapor cell. For example, the OPM may be sensitive to fields in the plane of the array, which, at least in some arrangements, can be tangential to the skull, for example, in applications for measurement of neural signals in the brain. MEG systems may also benefit from the ability to measure magnetic fields radial to the skull, for example, in applications for measurement of neural signals in the brain.

Figure 6A:
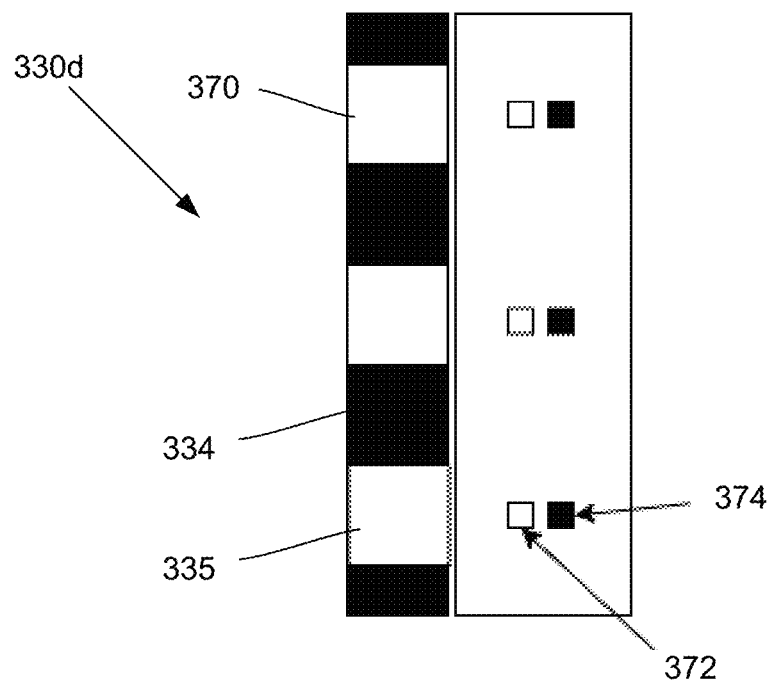
FIGS. 6A and 6B are, respectively, top and side views of a fourth embodiment of an array of optically pumped magnetometers, according to the invention.
Figure 6B:
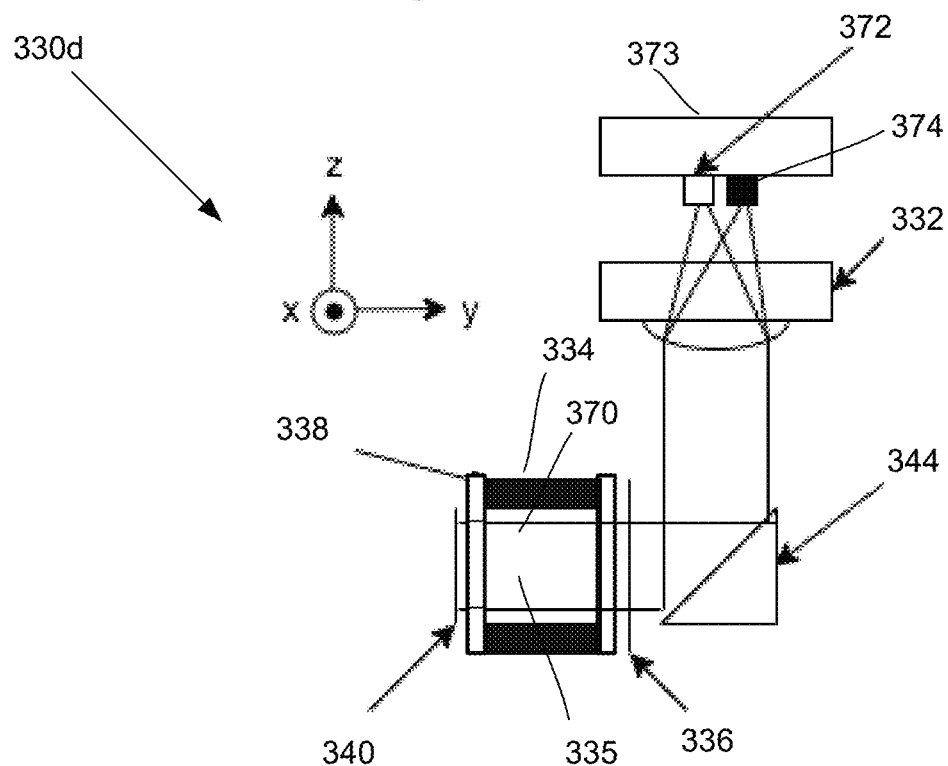

FIGS. 6A and 6B illustrates top and side views, respectively, of one embodiment of a linear array 330*d* of OPMs that may be particularly suitable for radial field measurements. This linear OPM array 330*d* includes the light sources 372, microlenses 332, vapor cells 370, quarter-wave plates 336, mirrors 340, magnetic field generator (not shown in FIGS. 6A and 6B, but similar to those illustrated in the preceding FIGS. 3A to 5B), and detectors 374 as described above. However, turning mirrors 344 are positioned between the microlenses 332 and the quarter-wave plates 336 to change the direction of the light from traveling along the z axis to traveling along the y axis (and vice versa on the return to the detectors 374). Otherwise, the embodiment of FIGS. 6A and 6B is the same as the embodiment of FIGS. 3A and 3B and all of the design options and microfabrication techniques are the same for both embodiments.

Figure 7A:
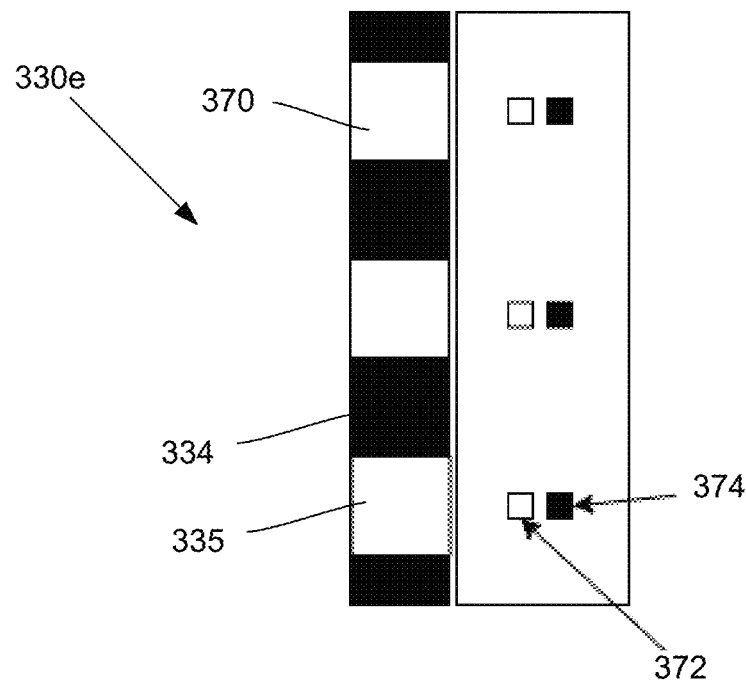
FIGS. 7A and 7B are, respectively, top and side views of a fifth embodiment of an array of optically pumped magnetometers, according to the invention.
Figure 7B:
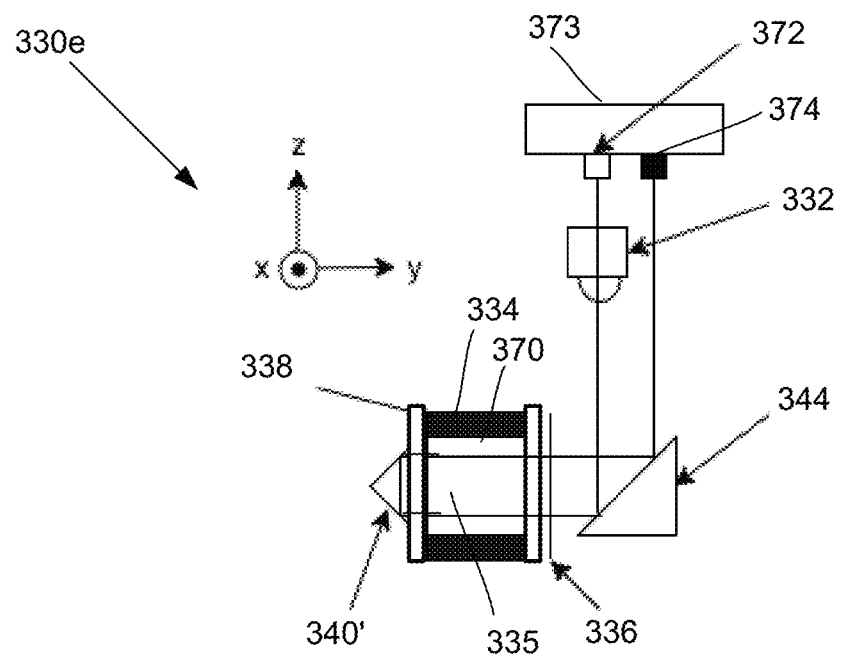

FIGS. 7A and 7B illustrates top and side views, respectively, of another embodiment of a linear array 330e of OPMs that may be particularly suitable for radial field measurements. This linear array 330e includes the light sources 372, microlenses 332, vapor cells 370, quarter-wave plates 336, mirrors 340', magnetic field generator (not shown in FIGS. 7A and 7B, but similar to those illustrated in the preceding FIGS. 3A to 5B), and detectors 374 as described above. As with the embodiment illustrated in FIGS. 6A and 6B, turning mirrors 344 are positioned between the microlenses 332 and the quarter-wave plates 336 to change the direction of the light from traveling along the z axis to traveling along the y axis (and vice versa on the return to the detectors 374). In addition, instead of flat mirrors, corner retro-reflectors 340' are used to send the light back toward the detectors 374. Optionally, the microlenses 332 are only disposed to receive light from the light source 372 and the light source may be aligned with the optical axis of the microlenses. This configuration may be advantageous in having non-overlapping beam paths inside the vapor cell. Otherwise, the embodiment of FIGS. 7A and 7B is the same as the embodiment of FIGS. 3A and 3B and all of the design options and microfabrication techniques are the same for both embodiments. It will be recognized that the retro-reflective mirrors 340' and smaller microlenses 332 can also be used in any of the other embodiments described herein in place of the flat mirror.

In at least some embodiments, these arrangements can provide high spatial resolution MEG with integrated arrays of optically pumped magnetometers. At least some embodiments may include a VCSEL array and a microlens array. At least some embodiments may include double pass absorption magnetometry due to the use of mirrors 340, 340'. At least some embodiments may include flattened solenoids as the magnetic field generator for high uniformity fields over a planar region.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. An array of optically pumped magnetometers, comprising:
   a vapor cell arrangement comprising a wafer defining one or more cavities and alkali metal atoms disposed in the one or more cavities to provide an alkali metal vapor;
   an array of light sources, each of the light sources arranged to illuminate a different portion of the one or more cavities of the vapor cell arrangement with light;
   at least one mirror arranged to reflect the light from the array of light sources after the light passes through the one or more cavities of the vapor cell arrangement;
   an array of detectors to receive light reflected by the at least one mirror, wherein each of the detectors is arranged to receive light originating from one of the light sources;
   an array of microlenses disposed between the light sources and the vapor cell arrangement, wherein each of the microlenses is configured to receive light from at least one of the light sources and at least one of the at least one mirror; and
   a single substrate, wherein the light sources and the detectors are all disposed on the single substrate.

2. The array of optically pumped magnetometers of claim 1, wherein the light sources and detectors are arranged in a plurality of pairs, each pair comprising one of the light sources and one of the detectors, wherein, for each of the pairs, the light source and the detector are positioned at opposite angles relative to an optical axis of a one of the microlenses that is arranged to receive light from the light source.

3. The array of optically pumped magnetometers of claim 1, wherein the microlenses are further configured to receive light reflected by the at least one mirror and to direct the reflected light to the detectors.

4. The array of optically pumped magnetometers of claim 1, further comprising at least one quarter-wave plate disposed between the light sources and the vapor cell arrangement to receive the light from the light sources prior to entry into the one or more cavities.

5. The array of optically pumped magnetometers of claim 1, further comprising a magnetic field generator disposed adjacent the vapor cell arrangement to generate a magnetic field within the one or more cavities.

6. The array of optically pumped magnetometers of claim 5, wherein the magnetic field generator is configured to independently generate magnetic fields in two orthogonal directions.

7. The array of optically pumped magnetometers of claim 1, wherein the at least one mirror is disposed within the one or more cavities.

8. The array of optically pumped magnetometers of claim 1, wherein the at least one mirror is disposed outside of the one or more cavities.

9. The array of optically pumped magnetometers of claim 1, wherein the one or more cavities is a plurality of cavities with each of the light sources arranged to illuminate a different one of the cavities.

10. The array of optically pumped magnetometers of claim 1, wherein the one or more cavities is a single cavity.

11. The array of optically pumped magnetometers of claim 1, wherein the array of optically pumped magnetometers is a two-dimensional array of optically pumped magnetometers.

12. The array of optically pumped magnetometers of claim 1, wherein the array of optically pumped magnetometers is a one-dimensional linear array of optically pumped magnetometers.

13. The array of optically pumped magnetometers of claim 12, further comprising a plurality of turning mirrors disposed between the light sources and the vapor cell arrangement to direct light from the light sources to the vapor cell arrangement.

14. The array of optically pumped magnetometers of claim 1, wherein the at least one mirror is a plurality of retroreflective mirrors.

15. A magnetic field measurement system, comprising:
   the array of optically pumped magnetometers of claim 1; and
   a computing device configured to receive signals from the detectors of the array of optically pumped magnetometers.

16. The magnetic field measurement system of claim 15, wherein the at least one mirror is a plurality of retroreflective mirrors.

17. The magnetic field measurement system of claim 15, wherein the array of optically pumped magnetometers further comprises a plurality of turning mirrors disposed between the light sources and the vapor cell arrangement to direct light from the light sources to the vapor cell arrangement.

18. A method of measuring a magnetic field, the method comprising:
   providing the array of optically pumped magnetometers of claim 1;
   illuminating the vapor cell arrangement using the light sources;
   in response to the illuminating, receiving signals from the detectors; and
   measuring the magnetic field using the signals.

\* \* \* \* \*